United States Patent
Li et al.

(10) Patent No.: US 8,748,383 B2
(45) Date of Patent: Jun. 10, 2014

(54) METHOD FOR TREATING BONE RELATED DISEASES AND CALCIUM DISORDERS

(71) Applicants: Shoufeng Li, Bridgewater, NJ (US); Anasuya Ashok Ghosh, Randolph, NJ (US); Simon D. Bateman, Randolph, NJ (US); Moise Azria, Basel (CH); Alan E. Royce, Saylorsburg, PA (US)

(72) Inventors: Shoufeng Li, Bridgewater, NJ (US); Anasuya Ashok Ghosh, Randolph, NJ (US); Simon D. Bateman, Randolph, NJ (US); Moise Azria, Basel (CH); Alan E. Royce, Saylorsburg, PA (US)

(73) Assignees: Novartis AG, Basel (CH); Emisphere Technologies, Inc., Cedar Knolls, NJ (US)

( * ) Notice: Subject to any disclaimer, the term of this patent is extended or adjusted under 35 U.S.C. 154(b) by 0 days.

(21) Appl. No.: 13/862,811

(22) Filed: Apr. 15, 2013

(65) Prior Publication Data

US 2013/0230593 A1     Sep. 5, 2013

Related U.S. Application Data

(60) Division of application No. 12/132,642, filed on Jun. 4, 2008, now Pat. No. 8,435,946, which is a continuation of application No. 10/564,259, filed as application No. PCT/EP2004/007584 on Jul. 9, 2004, now abandoned.

(60) Provisional application No. 60/486,495, filed on Jul. 11, 2003.

(51) Int. Cl.
*A61K 38/00* (2006.01)
*A61P 19/08* (2006.01)

(52) U.S. Cl.
USPC ....... 514/16.7; 514/11.9; 514/16.8; 514/16.9; 530/307

(58) Field of Classification Search
None
See application file for complete search history.

(56) References Cited

U.S. PATENT DOCUMENTS

| | | | | |
|---|---|---|---|---|
| 5,866,536 | A | 2/1999 | Leone-Bay et al. | |
| 5,952,008 | A | 9/1999 | Backstorm et al. | |
| 6,544,553 | B1 * | 4/2003 | Hsia et al. | 424/465 |
| 7,049,283 | B2 * | 5/2006 | Ault et al. | 514/11.9 |

FOREIGN PATENT DOCUMENTS

| | | |
|---|---|---|
| WO | 96/30036 | 10/1996 |
| WO | 00/54753 | 9/2000 |
| WO | 00/59863 | 10/2000 |
| WO | 01/47497 | 7/2001 |
| WO | 02/45754 | 5/2006 |

OTHER PUBLICATIONS

Leone-Bay A et al.,"Synthesis and Evaluation of Compounds that facilitate the Gastrointestinal Absorption of Heparin" Journal of Medicinal Chemistry, American Chemical Society, vol. 41, No. 7, pp. 1163-1171. (1998).

Leone-Bay et al., "Oral Delivery of Biologically Active Parathyroid Hormone", Pharmaceutical Research, New York, vol. 18, No. 7, pp. 964-970. (2001).

* cited by examiner

*Primary Examiner* — Robert Landsman
*Assistant Examiner* — Ian Dang
(74) *Attorney, Agent, or Firm* — Ann R. Pokalsky, Esq.; Dilworth & Barrese, LLP

(57) ABSTRACT

Solid pharmaceutical compositions and methods of their use suitable for the oral delivery of pharmacologically active agents, e.g. peptides, comprising a therapeutically-effective amount of a pharmacologically active agent; a crospovidone or povidone; and a delivery agent for said pharmacologically active agent are disclosed. The compositions utilize micronized forms of the delivery agent which provides enhanced bioavailability of pharmacologically active agents, particularly calcitonin.

10 Claims, No Drawings

METHOD FOR TREATING BONE RELATED DISEASES AND CALCIUM DISORDERS

This application is a divisional application of U.S. application Ser. No. 12/132,642, filed Jun. 4, 2008, now U.S. Pat. No. 8,435,946, which is a continuation of U.S. application Ser. No. 10/564,259, filed on Aug. 11, 2006, abandoned, which is a 371 application of PCT/EP2004/007584, filed July 9, 2004, which claims benefit of Provisional Application No. 60/486,495 filed on July 11, 2003, which in its entirety is herein incorporated by reference.

BACKGROUND OF THE INVENTION

1. Field of the Invention

The present invention relates to oral compositions for the delivery of pharmacologically active agents, to methods of enhancing the bioavailability of orally administered pharmacologically active agents, and to methods of treating and/or preventing disease in mammals, particularly humans, by orally administering a pharmacologically active agent in accordance with the invention.

2. Description of the Related Art

Oral delivery of pharmacologically active agents is generally the delivery route of choice since it is convenient, relatively easy and generally painless, resulting in greater patient compliance relative to other modes of delivery. However, biological, chemical and physical barriers such as varying pH in the gastrointestinal tract, powerful digestive enzymes, and active agent impermeable gastrointestinal membranes, makes oral delivery of some pharmacologically active agents to mammals problematic, e.g. the oral delivery of calcitonins, which are long-chain polypeptide hormones secreted by the parafollicular cells of the thyroid gland in mammals and by the ultimobranchial gland of birds and fish, has proven difficult due, at least in part, to the insufficient stability of calcitonin in the gastrointestinal tract as well as the inability of calcitonin to be readily transported through the intestinal walls into the blood stream.

U.S. Pat. Nos. 5,773,647 and 5,866,536 describe compositions for the oral delivery of active agents, such as heparin and calcitonin, with modified amino acids, such as, N-(5-chlorosalicyloyl)-8-aminocaprylic acid (5-CNAC), N-(10-[2-hydroxybenzoyl]aminodecanoic acid (SNAD), and N-(8-[2-hydroxybenzoyl]amino)caprylic acid (SNAC) In addition, WO 00/059863 discloses the disodium salts of formula I

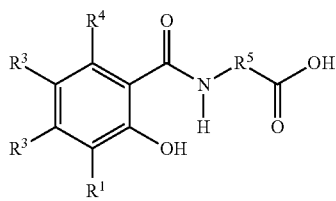

Formula I wherein $R^1$, $R^2$, $R^3$, and $R^4$ are independently hydrogen, —OH, —$NR^6R^7$, halogen, $C_1$-$C_4$alkyl, or $C_1$-$C_4$alkoxy;

$R^5$ is a substituted or unsubstituted $C_2$-$C_{16}$alkylene, substituted or unsubstituted $C_2$-$C_{16}$alkenylene, substituted or unsubstituted $C_1$-$C_{12}$alkyl(arylene), or substituted or unsubstituted aryl($C_1$-$C_{12}$alkylene); and $R^6$ and $R^7$ are independently hydrogen, oxygen, or $C_1$-$C_4$ alkyl; and hydrates and solvates thereof as particularly efficacious for the oral delivery of active agents, such as calcitonin, cyclosporin and heparin.

The present invention describes pharmaceutical compositions which provide still greater oral bioavailability of pharmacologically active agents, e.g. peptides such as calcitonin.

SUMMARY OF THE INVENTION

Accordingly, the present invention is directed to pharmaceutical compositions which, quite surprisingly, greatly enhance the oral bioavailability of active agents, particularly peptides. Specifically, the invention provides solid pharmaceutical compositions suitable for the oral delivery of pharmacologically active agents, comprising
1. a therapeutically-effective amount of a pharmacologically active agent;
2. pharmaceutically acceptable inactive excipients; and
3. a delivery agent for said pharmacologically active agent, wherein said delivery agent is in micronized form.

In another embodiment the present invention provides solid pharmaceutical compositions suitable for the oral delivery of calcitonin, comprising
1. a therapeutically-effective amount of a calcitonin; and
2. pharmaceutically acceptable inactive excipients, and
3. a delivery agent for said calcitonin, wherein said delivery agent is in micronized form.

In an additional embodiment of the present invention the pharmaceutically acceptable inactive excipient may be either or both of the polymers crospovidone or povidone.

In a still further embodiment of the present invention the solid pharmaceutical composition suitable for oral delivery may also comprise a diluent.

In addition in another embodiment of the present invention the solid pharmaceutical composition suitable for oral delivery may also comprise a lubricant.

In a further embodiment, the invention is directed to a method for enhancing the oral bioavailability of a pharmacologically active agent, said method comprising administering to a subject in need of said pharmacologically active agent an effective amount of a pharmaceutical composition according to the instant invention.

In a still further embodiment, the invention is directed to a method of treatment of bone related diseases and calcium disorders comprising administering to a patient in need of such treatment a therapeutically effective amount of a composition according to the instant invention, wherein said pharmacologically active agent is calcitonin.

Further features and advantages of the invention will become apparent from the following detailed description of the invention.

DETAILED DESCRIPTION OF THE INVENTION

The pharmacologically active agents suitable for use in the instant invention include both therapeutic as well as preventative agents and is directed particularly to agents which by themselves do not pass or which pass only a small amount of the administered dose through the gastro-intestinal mucosa and/or are susceptible to cleavage by acids and enzymes in the gastro-intestinal tract. The pharmacologically active agents include, but are not limited to proteins; polypeptides; hormones; polysaccharides including mixtures of mucopolysaccharides; carbohydrates; lipids; and combinations thereof.

Specific examples of pharmacologically active agents include, but are not limited to, the following, including synthetic, natural or recombinant sources thereof: growth hormone, including human growth hormones (hGH), recombinant human growth hormones (rhGH), bovine growth hormones, and porcine growth hormones; growth hormone-releasing hormones; interferons, including α, β, and γ-interferon; interleukin-1; interleukin-2; insulin, including porcine, bovine, human, and human recombinant, optionally having counter ions including sodium, zinc, calcium and ammonium; insulin-like growth factor, including IGF-1; heparin, including unfractionated heparin, heparinoids, dermatans, chondroitins, low, very low and ultra low molecular weight heparins; calcitonin, including salmon, porcine, eel, chicken and human; erythopoietein; atrial naturetic factor; antigens; monoclonal antibodies; somatostatin; protease inhibitors; adrenocorticotropin, gonadotropin releasing hormone; oxytocin; leutinizing-hormone-releasing hormone; follicle stimulating hormone; glucocerebrosidase; thrombopoietin; filgrastim; prostaglandins; cyclosporin; vasopressin; cromolyn sodium (sodium or disodium chromoglycate); vancomycin; desferrioxamine (DFO); parathyroid hormone (PTH), including its fragments; antimicrobials, including anti-fungal agents; vitamins; analogs, fragments, mimetics or polyethylene glycol (PEG)-modified derivatives of these compounds; or any combination thereof.

An interesting pharmacologically active agent is a pharmacologically active peptide, particularly bone active agents, and even more particularly calcitonin.

Bone active agents include classes of agents which display in vivo pharmacological activity in animals such as stabilization, healing, or growth of bone, deceleration or inhibition of bone turnover, deceleration or inhibition of bone resorption, inhibition of osteoclast activity, and stimulation of osteoblast activity. Some of these agents may be peptidic, for example calcitonins, parathyroid hormone (PTH), PTH fragments, analogs and releasers, and Transforming Growth Factors (TGFs) fragments, analogs and releasers. The bone active agents may also be small molecule non-peptidic structures which show in vivo pharmacological bone activities as described above in this paragraph.

A known class of such pharmacologically active agents, calcitonins, have varying pharmaceutical utility and are commonly employed in the treatment of e.g. Paget's disease, hypercalcemia and postmenopausal osteoporosis. Various calcitonins, including salmon, pig and eel calcitonin are commercially available and commonly employed for the treatment of e.g. Paget's disease, hypercalcemia of malignancy and osteoporosis. The calcitonin can be any calcitonin, including natural, synthetic or recombinant sources thereof, as well as calcitonin derivatives such as 1,7-Asu-eel calcitonin. The compositions can comprise a single calcitonin or any combination of two or more calcitonins. The preferred calcitonin is synthetic salmon calcitonin.

The calcitonins are commercially available or may be synthesized by known methods.

The amount of pharmacologically active agent is generally an amount effective to accomplish the intended purpose, e.g. a therapeutically effective amount. However, the amount can be less than that amount when a plurality of the compositions are to be administered, i.e., the total effective amount can be administered in cumulative dosage units. The amount of active agent can also be more than the effective amount when the composition provides sustained release of the pharmacologically active agent. The total amount of active agent to be used can be determined by methods known to those skilled in the art. However, because the compositions may deliver the active agent more efficiently than prior compositions, less amounts of active agent than those used in prior dosage unit forms or delivery systems can be administered to a subject while still achieving the same blood levels and/or therapeutic effects.

When the pharmacologically active agent is salmon calcitonin, the appropriate dosage will, of course, vary depending upon, for example, the host and the nature and severity of the condition being treated. However, in general, satisfactory results will be obtained systemically at daily dosages of from about 0.5 µg/kg to about 10 µg/kg animal body weight, preferably 1 µg/kg to about 6 µg/kg body weight.

The pharmacologically active agent generally comprises from 0.05 to 70 percent by weight relative to the total weight of the overall pharmaceutical composition, preferably an amount of from 0.01 to 50 percent by weight, more preferably 0.3 to 30 percent by weight relative to the total weight of the overall pharmaceutical composition.

The pharmaceutically acceptable inactive excipients may include polymers and inactive compounds which for example, aid the formulation or manufacturing of the solid oral dosage form contemplated by the present invention or which may aid the release of the solid oral composition in the gastro-intestinal environment.

The pharmaceutically inactive ingredients, referred to above, for example optionally include crospovidones and povidones, which may be any crospovidone and povidone. Crospovidone is a synthetic crosslinked homopolymer of N-vinyl-2-pyrrolidone, also called 1-ethenyl-2-pyrrolidinone, having a molecular weight of 1,000,000 or more. Commercially available crospovidones include Polyplasdone XL, Polyplasdone XL-10, Polyplasdone INF-10 available from ISP, Kollidon CL, available from BASF Corporation. The preferred crospovidone is Polyplasdone XL.

Povidone is a synthetic polymer consisting of linear 1-vinyl-2-pyrrolidinone groups having a molecular weight generally between 2,500 and 3,000,000. Commercially available povidones include Kollidon K-30, Kollidon K-90F available from BASF Corporation and Plasdone K-30 and Plasdone K-29/32, available from ISP.

As mentioned above, the crospovidones and povidones are commercially available. Alternatively, they may be synthesized by known processes.

The crospovidone, povidone or combination thereof is generally present in the compositions in an amount of from 0.5 to 50 percent by weight relative to the total weight of the overall pharmaceutical composition, preferably an amount of from 2 to 25 percent, more preferably 5 to 20 percent by weight relative to the total weight of the pharmaceutical composition.

The delivery agents useful in the present invention are any agents useful for delivering the particular pharmacologically active agent. Suitable delivery agents are any one of the 123 modified amino acids disclosed in aforementioned U.S. Pat. No. 5,866,536 or any one of the 193 modified amino acids described in the aforementioned U.S. Pat. No. 5,773,647 or any combination thereof. The contents of the aforementioned U.S. Pat. Nos. 5,773,647 and 5,866,536 are hereby incorporated by reference in their entirety. In addition, the delivery agent can be the disodium salt of any of the aforementioned modified amino acids as well as ethanol solvates and hydrates thereof. Suitable compounds include compounds of the following formula I

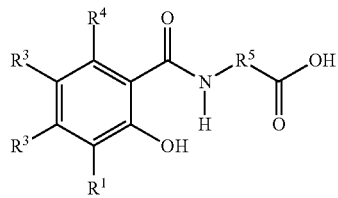

Formula I wherein

R¹, R², R³, and R⁴ are independently hydrogen, —OH, —NR⁶R⁷, halogen, $C_1$-$C_4$alkyl, or $C_1$-$C_4$alkoxy;

R⁵ is a substituted or unsubstituted $C_2$-$C_{16}$alkylene, substituted or unsubstituted $C_2$-$C_{16}$alkenylene, substituted or unsubstituted $C_1$-$C_{12}$alkyl(arylene), or substituted or unsubstituted aryl($C_1$-$C_{12}$alkylene); and R⁶ and R⁷ are independently hydrogen, oxygen, or $C_1$-$C_4$ alkyl; and hydrates and alcohol solvates thereof. The compounds of formula I as well as their disodium salts and alcohol solvates and hydrates thereof are described in WO 00/059863, along with methods for preparing them.

The disodium salt may be prepared from the ethanol solvate by evaporating or drying the ethanol solvate by methods known in the art to form the anhydrous disodium salt. Drying is generally carried out at a temperature of from about 80 to about 120° C., preferably from about 85 to about 90° C., and most preferably at about 85° C. The drying step is generally performed at a pressure of 26" Hg or greater. The anhydrous disodium salt generally contains less than about 5% by weight of ethanol and preferably less than about 2% by weight of ethanol, based on 100% total weight of anhydrous disodium salt.

The disodium salt of the delivery agent can also be prepared by making a slurry of the delivery agent in water and adding two molar equivalents of aqueous sodium hydroxide, sodium alkoxide or the like. Suitable sodium alkoxides include, but are not limited to, sodium methoxide, sodium ethoxide, and combinations thereof.

A still further method of preparing the disodium salt is by reacting the delivery agent with one molar equivalent of sodium hydroxide to yield the disodium salt.

The disodium salt can be isolated as a solid by concentrating the solution containing the disodium salt to a thick paste by vacuum distillation. This paste may be dried in a vacuum oven to obtain the disodium salt of the delivery agent as a solid. The solid can also be isolated by spray drying an aqueous solution of the disodium salt.

The delivery agents may be prepared by methods known in the art, e.g., as mentioned above, by methods described in U.S. Pat. Nos. 5,773,647 and 5,866,536.

The ethanol solvates, as described in the aforementioned WO 00/059863, include, but are not limited to, a molecular or ionic complex of molecules or ions of ethanol solvent with molecules or ions of the disodium salt of the delivery agent. Typically, the ethanol solvate contains about one ethanol molecule or ion for every molecule of disodium salt of the delivery agent.

The ethanol solvate of the disodium salt of the delivery agent can be prepared by dissolving the delivery agent in ethanol. Typically, each gram of delivery agent is dissolved in from about 1 to about 50 mL of ethanol and generally, from about 2 to about 10 mL of ethanol. The delivery agent/ethanol solution is then reacted with a molar excess of a sodium containing salt, such as a monosodium containing salt, relative to delivery agent, i.e. for every mole of delivery agent there is more than one mole of sodium cations, yielding the ethanol solvate. Suitable monosodium salts include, but are not limited to, sodium hydroxide; sodium alkoxides, such as sodium methoxide and sodium ethoxide; and any combination of the foregoing. Preferably, at least about two molar equivalents of the monosodium containing salt are added to the ethanol solution, i.e. for every mole of delivery agent there is at least about two moles of sodium cations. Generally, the reaction is performed at or below the reflux temperature of the mixture, such as at ambient temperature. The ethanol solvate is then recovered by methods known is the art, such as, concentration of the resulting slurry at atmospheric distillation, cooling the concentrated slurry and filtering the solid. The recovered solid can then be vacuum dried to obtain the ethanol solvate.

The hydrates of the disodium salts of the delivery agents may be prepared by drying the ethanol solvate to from an anhydrous disodium salt, as described above, and hydrating the anhydrous disodium salt. Preferably, the monohydrate of the disodium salt is formed. Since the anhydrous disodium salt is very hydroscopic, the hydrate forms upon exposure to atmospheric moisture. Generally, the hydrating step is performed at from about ambient temperature to about 50° C., preferably ambient temperature to about 30° C. and in an environment having at least 50% relative humidity. Alternatively, the anhydrous disodium salt may be hydrated with steam.

The preferred delivery agents are N-(5-chlorosalicyloyl)-8-aminocaprylic acid (5-CNAC), N-(10-[2-hydroxybenzoyl] amino)decanoic acid (SNAD), N-(8-[2-hydroxybenzoyl] amino)caprylic acid (SNAC) and their monosodium and disodium salts, ethanol solvates of their sodium salts and the monohydrates of their sodium salts and any combinations thereof. The most preferred delivery agent is the disodium salt of 5-CNAC and the monohydrate thereof.

The delivery agent, 5 CNAC, SNAD, and SNAC are very water soluble and nearly fully, i.e. greater than 90%, absorbed by the gastro-intestinal tract whether it is ingested in micronized or coarse form. However, it has been found, surprisingly, that when a micronized form of one of these carrier agents is employed in the composition, the absorption of the pharmacologically active agent of the present composition is more completely absorbed into the blood stream. Therefore, the use of micronized carrier agent is a required element of the present invention.

A micronized form of the carrier agent, which is utilized in preparation of the solid oral dosage form of the present invention, is defined as a carrier agent which, when added to the present composition mixture of pharmacologically active agent and pharmaceutically inactive ingredients, has an average particle size of less than 40 micrometers. Desirably the carrier agent of the present invention has a micronized form which is defined as an average particle size of less than 20 microns. More interestingly, the carrier agent for the present invention has a micronized form which is defined as an average particle size of less than 10 microns.

Micronized forms of the carrier agent of the present invention may be prepared by grinding it in a grinding mill which is acceptable for grinding pharmaceutical ingredients and which is capable of grinding the pharmaceutical ingredients and/or carrier agent to a fine and uniform micronized particle size. An example of such a grinding mill is an Air Jet Mill Gem T® (Copley Scientific, Ltd., Nottingham, UK). The finely ground carrier agent either separately or finely ground carrier agent plus any combination of finely ground additional ingredients of the present invention may then be screened, for example, over a mesh screen having the appropriate openings, in order to allow only those ingredients which have the required particle size to pass through and be collected for use in the present invention.

The pharmaceutical compositions of the present invention typically contain a delivery effective amount of one or more of the delivery agents, i.e. an amount sufficient to deliver the active agent for the desired effect. Generally, the delivery agent is present in an amount of 2.5% to 99.4% by weight, more preferably 25% to 50% by weight.

The pharmaceutical compositions of the present invention may be provided as a capsule including a soft-gel capsule, tablet, caplet or other solid oral dosage form, all of which can be prepared by methods well known in the art.

The compositions may additionally comprise additives in amounts customarily employed including, but not limited to, a pH adjuster, a preservative, a flavorant, a taste-masking agent, a fragrance, a humectant, a tonicifier, a colorant, a surfactant, a plasticizer, a lubricant such as magnesium stearate, a flow aid, a compression aid, a solubilizer, an excipient, a diluent such as microcrystalline cellulose, e.g. Avicel PH 102® (supplied by FMC corporation 1735 Market Street Philadelphia, Pa. 19103, USA), or any combination thereof. Other additives may include phosphate buffer salts, citric acid, glycols, and other dispersing agents.

The composition may also include one or more enzyme inhibitors, such as actinonin or epiactinonin and derivatives thereof; aprotinin, Trasylol and Bowman-Birk inhibitor.

Further, a transport inhibitor, i.e. a ρ-glycoprotein such as Ketoprofin, may be present in the compositions of the present invention.

Preferably, the solid pharmaceutical compositions of the instant invention include a diluent, such as Avicel®, and a lubricant, such as magnesium stearate.

The solid pharmaceutical compositions of the instant invention can be prepared by first grinding either the carrier agent or the carrier agent with any combination of the additional ingredients of the present composition to a micronized particle size. The micronized carrier agent or micronized carrier agent plus micronized additional ingredients of the present invention may then be further processed by conventional methods e.g. by blending a mixture of the active agent or active agents, the delivery agent, the crospovidone or povidone and other ingredients, kneading, and filling into capsules or, instead of filling into capsules, molding followed by further tableting or compression-molding to give tablets. In addition, a solid dispersion may be formed by known methods followed by further processing to form a tablet or capsule.

Preferably, the ingredients in the pharmaceutical compositions of the instant invention are homogeneously or uniformly mixed throughout the solid dosage form.

The compositions of the present invention may be administered to deliver an active agent to any animal in need thereof, including, but not limited to, mammals, such as rodents, cows, pigs, dogs, cats, and primates, particularly humans.

The following examples serve to further illustrate the invention and will be readily understood by one of ordinary skill in the art. The examples are not meant to be limiting of the present invention in any way.

EXAMPLE 1

Micronized 5-CNAC and tablets of salmon calcitonin plus micronized 5-CNAC may be prepared in accordance with the present invention as follows:

Preparation of Micronized 5-CNAC

Coarse 5-CNAC, which is to be micronized, is added to a jet mill (Air Jet Mill Gem T® Copley Scientific, Ltd., Nottingham, UK) using a 80 ceramic pan cake jet mill, 8 cm diameter, 6 bar N2, 0.5 mm nozzles with manual feed of about 700 g/h. The coarse 5-CNAC is jet milled and periodically sampled under microscope with reference ruler measurements to identify when the average desired micronized particle size is obtained. Three different batches are ground to create 6 um, 35 um, and 46 um batches. Individual sieving of the separate micronized batches is then done by using a conical sieve mill (Quadro Comil, Quadro Engineering Incorporated 613 Colby Drive, Waterloo, Ontario, Canada N2V 1A1) with a U10, 813 um conical sieve, round beater, operating at 1500 upm with throughput of about 150 kg/h.

Formulation I. Salmon Calcitonin Formulation with 5-CNAC of Different Particle Size

| Ingredient | Amount (mg) | Percent (%) |
| --- | --- | --- |
| Salmon Calcitonin | 1 | 0.25 |
| Micronized 5-CNAC | 228 | 57 |
| Avicel PH 102 ® | 147 | 36.75 |
| Crospovidone, NF | 20 | 5 |
| Magnesium stearate | 4 | 1 |
| Total | 400 | 100 |

Preparation of Formulation 1

Three different batches of tablets are prepared using the three different batches of micronized 5-CNAC disodium, one tablet batch having an average 5-CNAC disodium particle size of 46 microns (Batch A), a second tablet batch having an average 5-CNAC disodium particle size of 6 microns (Batch B), and a third tablet batch having an average 5-CNAC disodium particle size of 35 microns (Batch C).

0.50 g of salmon calcitonin, pre-screened through a 40 mesh screen, 57. g of micronized 5-CNAC disodium salt, screened through a 35 mesh screen, and 10 g of Polyplasdone XL (crospovidone, NF, International Specialty Products, 1361 Alps Road, Wayne, N.J., 07470, USA) is combined in a 500 mL jar and is mixed using a Turbula mixer for 100 revolutions at a speed of 46 RPM. An additional 57. g of micronized 5-CNAC disodium salt, screened through a 35 mesh screen, and 36.75 g of Avicel PH 102® is added to the jar and mixed for 500 revolutions at a speed of 46 RPM. A further 36.75 g of Avicel PH 102® is added to the jar and is mixed for an additional 100 revolutions at a speed of 46 RPM. 4.0 g of magnesium stearate is screened into the jar using a 35 mesh screen and is blended for 1 minute at a speed of 46 RPM. The final blend is compressed into tablets using a Manesty B3B tablet press. The tablet weight is approximately 400 mg.

The bioavailability of the tablets created in Example 1 may be tested as follows:

EXAMPLE 2

Primate Administration

The tablets are prepared as in Example 1 using three different batches of micronized 5-CNAC disodium, one tablet batch having an average 5-CNAC disodium particle size of 46 microns (Batch A), a second tablet batch having an average 5-CNAC disodium particle size of 6 microns (Batch B), and a third tablet batch having an average 5-CNAC disodium particle size of 35 microns (Batch C). The tablets prepared from each of the three different batches are administered to the same four Rhesus monkeys separately on different days as follows:

The Rhesus monkeys fast overnight prior to dosing and are restrained in chairs fully conscious, for the duration of the study period. One tablet from Batch A or Batch B or Batch C is administered to each monkey via a gavage tube followed by 10 mL of water.

Rhesus monkey blood samples are collected immediately before administration and at 0.25, 0.5, 0.75, 1, 1.5, 2, 3, 4, 5, and 6 hours after administration. A tablet from each of the remaining two tablet batches is dosed and blood samples are collected in a similar manner but on a separate day for each of the remaining tablet batches. Resulting plasma salmon calcitonin for each dose and for each monkey is determined by radioimmunoassay. For each monkey, the primate plasma salmon calcitonin (SCt) for one batch and one time period, mean plasma SCt concentrations for all monkeys for one batch and one time period, Standard Deviation (SD) of plasma SCt concentrations for one batch and one time period, and Standard Error of the Mean (SEM) for plasma SCt concentrations for all monkeys for one batch and one time period are calculated and reported in Tables 1, 2, and 3 as follows.

The foregoing clearly shows that the compositions according to the instant invention allow considerably improved oral bioavailability of active agent. The improved bioavailability results in high in vivo concentrations of active agent, particularly calcitonin, being achieved via oral delivery, and in correlation to the particle sizes of 5-CNAC in the oral formulations of the Examples.

The foregoing embodiments and examples are given merely to illustrate the instant invention and are not intended to be limiting. Numerous other embodiments and variations are within the scope of the invention and readily accessible to those skilled in the art.

The invention claimed is:

1. A method for treating bone related diseases and calcium disorders, said method comprising: administering to a patient in need of such treatment a pharmaceutical composition comprising:

TABLE 1

BATCH A: AVERAGE 5-CNAC PARTICLE SIZE 46 MICROMETERS
Salmon Calcitonin (SCt) Plasma Concentrations [pg/mL]
(Single Oral Tablet (200 mg 5-CNAC + 1 mg SCt) to the Rhesus Monkey)

| Animal no. | Time [hours] | | | | | | | | | | |
|---|---|---|---|---|---|---|---|---|---|---|---|
| | 0 | 0.25 | 0.50 | 0.75 | 1 | 1.5 | 2 | 3 | 4 | 5 | 6 |
| 1 | 0.0 | 17.8 | 91.7 | 279.7 | 449.2 | 278.8 | 48.0 | 10.5 | 5.3 | 3.3 | 0.0 |
| 2 | 0.0 | 117.4 | 535.0 | 430.8 | 981.4 | 1718.0 | 2396.4 | 719.5 | 253.6 | 102.1 | 62.9 |
| 3 | 0.0 | 113.9 | 754.5 | 1502.0 | 2351.0 | 2066.0 | 2684.4 | 1310.0 | 649.6 | 280.6 | 156.5 |
| 4 | 0.0 | 46.0 | 127.0 | 425.5 | 765.8 | 1102.0 | 1599.0 | 1022.0 | 419.3 | 87.0 | 23.4 |
| Mean | 0.0 | 73.8 | 377.1 | 659.5 | 1136.9 | 1291.2 | 1682.0 | 765.5 | 332.0 | 118.3 | 60.7 |
| SD | 0.0 | 49.7 | 322.2 | 566.0 | 838.4 | 783.8 | 1182.1 | 558.1 | 271.6 | 116.6 | 68.9 |
| SEM | 0.0 | 24.9 | 161.1 | 283.0 | 419.2 | 391.9 | 591.0 | 279.0 | 135.8 | 58.3 | 34.5 |

Lower Limit of Quantification (LLOQ) = 2.5 pg/mL, concentrations below LLOQ were set to zero for Table 1

TABLE 2

BATCH B: AVERAGE 5-CNAC PARTICLE SIZE 6 MICROMETERS
Salmon Calcitonin (SCt) Plasma Concentrations [pg/mL]
(Single Oral Tablet (200 mg 5-CNAC + 1 mg SCt) to the Rhesus Monkey)

| Animal no. | Time [hours] | | | | | | | | | | |
|---|---|---|---|---|---|---|---|---|---|---|---|
| | 0 | 0.25 | 0.50 | 0.75 | 1 | 1.5 | 2 | 3 | 4 | 5 | 6 |
| 1 | 0.0 | 265.6 | 315.8 | 245.6 | 357.2 | 1927.0 | 3010.0 | 863.2 | 139.4 | 48.5 | 20.8 |
| 2 | 0.0 | 607.0 | 777.0 | 1336.0 | 1602.0 | 4146.0 | 7521.0 | 2681.0 | 420.8 | 73.9 | 43.2 |
| 3 | 0.0 | 80.9 | 225.5 | 325.6 | 655.6 | 1478.0 | 3979.0 | 2775.0 | 520.2 | 91.5 | 41.3 |
| 4 | 0.0 | 286.4 | 155.3 | 237.7 | 241.0 | 269.7 | 294.2 | 321.0 | 179.8 | 67.5 | 13.6 |
| Mean | 0.0 | 310.0 | 368.4 | 536.2 | 714.0 | 1955.2 | 3701.1 | 1660.1 | 315.1 | 70.4 | 29.7 |
| SD | 0.0 | 218.5 | 280.2 | 534.7 | 617.2 | 1619.6 | 2986.3 | 1253.5 | 184.8 | 17.8 | 14.8 |
| SEM | 0.0 | 109.2 | 140.1 | 267.3 | 308.6 | 809.8 | 1493.1 | 626.7 | 92.4 | 8.9 | 7.4 |

Lower Limit of Quantification (LLOQ) = 2.5 pg/mL, concentrations below LLOQ were set to zero for Table 2

TABLE 3

BATCH C: AVERAGE 5-CNAC PARTICLE SIZE 35 MICROMETERS
Salmon Calcitonin (SCt) Plasma Concentrations [pg/mL]
(Single Oral Tablet (200 mg 5-CNAC + 1 mg SCt) to the Rhesus Monkey)

| Animal no. | Time [hours] | | | | | | | | | | |
|---|---|---|---|---|---|---|---|---|---|---|---|
| | 0 | 0.25 | 0.50 | 0.75 | 1 | 1.5 | 2 | 3 | 4 | 5 | 6 |
| 1 | 0.0 | 36.1 | 94.7 | 428.0 | 739.4 | 2568.0 | 4025.0 | 1348.0 | 499.6 | 218.4 | 98.1 |
| 2 | 0.0 | 10.9 | 55.0 | 168.9 | 248.2 | 507.3 | 654.0 | 434.8 | 177.3 | 68.8 | 38.9 |
| 3 | 0.0 | 172.3 | 336.6 | 409.5 | 584.9 | 1487.0 | 2087.0 | 1479.0 | 162.0 | 52.0 | 17.2 |
| 4 | 0.0 | 7.9 | 46.9 | 208.1 | 390.1 | 1237.0 | 2347.0 | 1342.0 | 192.3 | 42.3 | 19.2 |
| Mean | 0.0 | 56.8 | 133.3 | 303.6 | 490.7 | 1449.8 | 2278.3 | 1151.0 | 257.8 | 95.4 | 43.4 |
| SD | 0.0 | 78.0 | 137.1 | 134.1 | 215.8 | 853.5 | 1382.1 | 481.6 | 161.7 | 82.7 | 37.8 |
| SEM | 0.0 | 39.0 | 68.6 | 67.1 | 107.9 | 426.7 | 691.1 | 240.8 | 80.8 | 41.4 | 18.9 |

Lower Limit of Quantification (LLOQ) = 2.5 pg/mL, concentrations below LLOQ were set to zero for Table 3 a. a therapeutically effective amount of calcitonin
b. a pharmaceutically acceptable inactive excipient, and
c. a delivery agent of formula I for said calcitonin

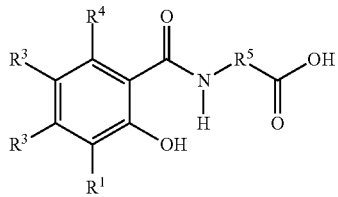

Formula I wherein
- $R^1$, $R^2$, $R^3$, and $R^4$ are independently hydrogen, —OH, —$NR^6R^7$, halogen, $C_1$-$C_4$alkyl, or $C_1$-$C_4$alkoxy;
- $R^5$ is a substituted or unsubstituted $C_2$-$C_{16}$alkylene, substituted or unsubstituted $C_2$-$C_{16}$alkenylene, substituted or unsubstituted $C_1$-$C_{12}$alkyl(arylene), or substituted or unsubstituted aryl($C_1$-$C_4$alkylene); and
- $R^6$ and $R^7$ are independently hydrogen, oxygen, or $C_1$-$C_4$ alkyl; and hydrates, pharmaceutically acceptable salts and solvates thereof, wherein said delivery agent is in micronized form and has an average particle size of less than 10 microns.

2. The method of claim 1 wherein the calcitonin is salmon calcitonin.

3. The method of claim 1 wherein said inactive excipient is selected from the group consisting of crospovidone and povidone.

4. The method of claim 1, wherein the delivery agent is selected from the group consisting of N-(5-chlorosalicyloyl)-8-aminocaprylic acid (5-CNAC), N-(10-[2-hydroxybenzoly] amino)decanoic acid (SNAD), N-(8-[2-hydroxybenzoyl] amino)caprylic acid (SNAC) and disodium salts thereof.

5. The method according to claim 4, wherein the delivery agent is selected from the group consisting of a disodium salt of 5-CNAC, a disodium salt of SNAD, and a disodium salt of SNAC.

6. The method of claim 1 wherein the pharmaceutical composition further comprises a diluent.

7. The method of claim 6 wherein the diluent is microcrystalline cellulose.

8. The method of claim 1 wherein the pharmaceutical composition further comprises a lubricant.

9. The method of claim 8 wherein the lubricant is magnesium stearate.

10. The method of claim 5, wherein the delivery agent is the disodium salt of 5-CNAC.

* * * * *